United States Patent [19]

Fruman et al.

[11] 4,316,383
[45] Feb. 23, 1982

[54] APPARATUS FOR MEASURING THE REPRESENTATIVE PARAMETERS OF RHEOLOGICAL PROPERTIES OF VISCOELASTIC FLUIDS

[75] Inventors: Daniel Fruman, Le Pecq, France; Marshall Tulin, Chevy Chase, Md.

[73] Assignee: Agence Nationale de Valorisation de la Recherche (ANVAR), France

[21] Appl. No.: 111,727

[22] Filed: Jan. 14, 1980

[30] Foreign Application Priority Data

Jan. 12, 1979 [FR] France .................. 79 00788

[51] Int. Cl.³ ........................................ G01N 11/08
[52] U.S. Cl. ................................................. 73/55
[58] Field of Search ........................... 73/55, 56, 54

[56] References Cited

U.S. PATENT DOCUMENTS 1,529,811  3/1925  Priest ........................ 73/56
3,766,773  10/1973  Limpert ..................... 73/56
3,908,442  9/1975  Chmiel ...................... 73/55

FOREIGN PATENT DOCUMENTS 922204  1/1947  France ...................... 73/55

*Primary Examiner*—Gerald Goldberg
*Assistant Examiner*—Joseph W. Roskos
*Attorney, Agent, or Firm*—Sandler & Greenblum

[57] ABSTRACT

Apparatus for determining rheological parameters of viscoelastic fluids is provided. The apparatus comprises two similar cylinder-piston assemblies ending at identical flow orifices. The pistons are pushed conjointly by a motor at an adjusted speed. A differential manometer is arranged between the cylinders immediately upstream of the orifices. One of the cylinders contains fluid to be studied and the other a Newtonian comparison fluid. The strain rates of the fluids are defined by the adjusted flow rates, and the pressure differential expresses elongation stress of the viscoelastic fluid. This apparatus is applicable in the rheological study of dilute solutions of macromolecular compositions.

22 Claims, 7 Drawing Figures

APPARATUS FOR MEASURING THE REPRESENTATIVE PARAMETERS OF RHEOLOGICAL PROPERTIES OF VISCOELASTIC FLUIDS

BACKGROUND OF THE INVENTION

1. Field of the Invention

The invention relates to an apparatus adapted to determine the representative parameters of rheological properties of viscoelastic fluids, particularly dilute solutions of macromolecular compositions, the apparatus translating the variations of behaviour during flow in comparison to Newtonian fluids by means of the relationship between stress and strain rate.

2. Discussion of Prior Art

It is noted that, in fluid mechanics, a fluid in which the relation between the stress tensor and the strain rate tensor, or the behavioural law, is linear. It will be remembered that a stress, expressing the force applied to a portion of fluid surface, is to have the dimensions of pressure, while a strain rate, expressing a velocity gradient, is expressed as the inverse of time. Finally, the ratio of stress to strain rate is a dynamic viscosity. In an isotropic Newtonian fluid, the viscosity is a constant depending uniquely on the temperature and the pressure. More precisely, the stresses are proportional to the rate of shear.

A vast number of fluids do not obey this simple behavioural law relating stress and strain rate. It is thus necessary to complement the Newtonian term of the behavioural law by a supplemental term taking into account the presence of additional stresses. In the case of fluids having complex behavior, such as solutions of macromolecular compositions, the additional stresses are a function on one hand of the relative difference between the inverse of the maximum strain rate and the relaxation time of the macromolecular composition and on the other hand of a stress which expresses the intensity of forces transmitted to the fluid by the macromolecular composition in the course of its deformation. This type of behavior is known as viscoelastic. In general, for low strain rates, the behavior of these fluids is practically Newtonian.

This has been observed particularly for macromolecular composition solutions which are formed by polymerization of basic units into long chains.

Studies have been published in scientific literature, relating to the anomalies of non-turbulent flows, in the steady state as solutions of macromolecular compositions of elevated molecular weights having elastic chains, such as polyethylene oxides. It appears that generally these anomalies manifest themselves when fluid, at least in certain regions, is subjected to extensional deformation. Such flows have been achieved at the stagnation point of Pitot tube sensors, at the inlet and at the outlet of an orifice, and in a flow in front of and around an obstacle having a progressive curvature, such as a circular cylinder. It appears that the presence of a macromolecular composition introduces significant variations from the fields of flow and pressure of the types of flow mentioned. In the case of a Pitot tube, the stagnation pressure can be smaller than the dynamic pressure. In flows across orifices, the necessary driving pressure to establish a given flow can become greater than that which is required by a Newtonian fluid of equal flow rate. The drag of a circular cylinder of small diameter can clearly be greater than the drag in the solvent, etc. The Pitot tube and the orifices offer the advantage of permitting the taking of simple quantitative measurements which can be related to rheological parameters of the fluid. For measurements with a Pitot tube, one drives, for example, a probe over a circular trajectory at the end of a turning arm. For measurements of flow across an orifice, one measures the differential pressure between the fluid immediately upstream and downstream of the orifice for a given flow, readily obtained by pressurizing the liquid with a piston having a given velocity of displacement in a cylinder of known cross-section.

The compilation of published studies, and particularly those which utilize the Pitot tube technique and that of the flow in an orifice, show that for solutions of polyethylene oxide having an elevated molecular weight, pressure anomalies begin to appear at the critical values of the strain rate, and, furthermore, that the increase in abnormal pressure is proportional to the excess of the strain rate over the critical values. The critical values and the coefficients of proportionality are functions of the concentration of the macromolecular composition. These results imply that the behavior during flow of diluted solutions of macromolecular compositions of the type referred to above can be defined by two parameters, both of which are functions of the concentration; a relaxation time and a specific stress. The specific stress is proportional to the concentration for sufficiently high dilutions. This behavior conforms to that of a theoretical model which is based upon the hypothesis that elastic molecules do not extend to a significant extent except at strain rates greater than the critical value, and that they orient themselves along a preferred direction adjacent to that of the principal strain rate.

The devices utilized in published studies make it possible to determine couples of correlated values, the values of one couple being respectively representative of a strain rate and of a corresponding pressure. The results on a rectangular coordinate graph of value couples yield points from which a representative curve can be traced. This curve causes the appearance, beyond a particular value of strain rate called the critical strain rate, of abnormal behavior of solutions of macromolecular compositions. The determination of the critical strain rate suffers from imprecision, particularly when the solution is very dilute and when this behavior is close, by virtue of the low value of the specific stress, to Newtonian behavior. This is also true for concentrated solutions or slightly dilute solutions of certain polymers for which the transition between Newtonian and abnormal behavior is progressive.

SUMMARY OF THE INVENTION

The invention has as an object an apparatus for the determination of representative parameters of rheological properties of viscoelastic fluids having a precision of measurement results which is improved in significant fashion with respect to devices in the present state of the art.

The invention also has as an object an apparatus of simple and economical design, which allows the rapid analysis of measurements and which is adapted for use in diverse applications.

To this end, the invention proposes an apparatus adapted for the determination of representative parameters of rheological properties of viscoelastic fluids, particularly dilute solutions of macromolecular compositions, translating the variation of flow behavior with respect to a Newtonian fluid from the relation between stress and strain rate, the apparatus comprising means for forcing a fluid across a calibrated flow orifice, means for adjusting the flow rate of fluid across the orifice, and means for measuring the pressure drop of the fluid across the orifice. The said forcing means comprise a pair of similar cylinders with the calibrated flow orifice at the end and a pair of pistons sliding in the cylinders and pushed conjointly towards the end by a motor. Blockable filling means are provided for connecting each cylinder to a respective fluid reservoir and the flow rate adjustment means comprise a control means coupled to the motor and adapted to adjust the speed of piston strokes. The pressure drop measurement means comprise differential pressure measurement means between two inlets connected respectively to each cylinder immediately upstream of the calibrated orifices. Correlating registration means of given couples are respectively connected by control means and to the differential pressure measurement means.

By virtue of the identity of the cross-section of the cylinders and of the orifices and of the conjoined piston strokes by the motor, the speed in the flow orifices are exactly the same. The differential pressure measurement means between the upstreams of the orifices make it possible to attain the differential flow stress. Therefore, if one of the two cylinders is filled with viscoelastic fluid which is being studied, and the other cylinder is filled with a Newtonian fluid whose viscosity is adjusted to be equal to the viscosity of the viscoelastic fluid in the range of Newtonian behavior, the differential stress registered will be representative of the viscoelastic abnormality, that is to say the stress elongation. In the case of the study of viscoelastic properties of a solution, one would utilize as a Newtonian fluid the solvent of the solution to which is added a known solute to provide Newtonian behavior in solution. The appropriate quantity of solute will be adjusted to obtain a zero differential pressure at low stroke speed. This having been obtained, one will increase by successive steps the stroke speed to determine the critical strain rate and the curve of abnormal stress.

It is often preferable to operate in flows having a submerged jet. Each cylinder then comprises a cylindrical collector extending from the cylinder beyond the calibrated orifice and is provided with an evacuation nozzle with a position above the collector. A means for measuring differential pressure is connected between the collectors, in a fashion so as to bring a pressure difference into play downstream of the orifices; this is subtracted from the pressure difference upstream to display the effective abnormal pressure.

Preferably, the cylinders are arranged so that they have horizontal axes and the collectors are orientable around this axis to make it possible to place the nozzles at the lower level of the collectors, and to thus operate with a free jet.

In a preferred arrangement, the cylinders are equipped with jackets in which a fluid of regulated temperature is circulated. The parameters which are to be determined are variable with the temperature, such that the measurements must be made at a constant and known temperature.

Preferably the flow orifices are provided in removeable diaphragms having cross-sections which are circular, rectangular, elongated or annular. These latter shapes correspond to bi-dimensional flows and are better adapted for certain types of fluids.

In a preferred embodiment, the control means coupled to the motor comprises a programmer element which sets a sequence of stroke speeds at discrete increasing values. Each speed corresponds to an established regime; one thus obtains successive points of the curve which are automatically run.

The registration means preferably comprise analog/numeric converters coupled to the speed control means and to each of the differential pressure measurement means of, memory means coupled to the converters and reading and display means coupled to the memory means. This allows for numeric exploitation of the measurement results.

BRIEF DESCRIPTION OF THE DRAWINGS

The characteristics and advantages of the invention will further appear from the description which follows, by way of example, with reference to the annexed drawings, in which.

DETAILED DESCRIPTION OF THE DRAWINGS

Figure 1:
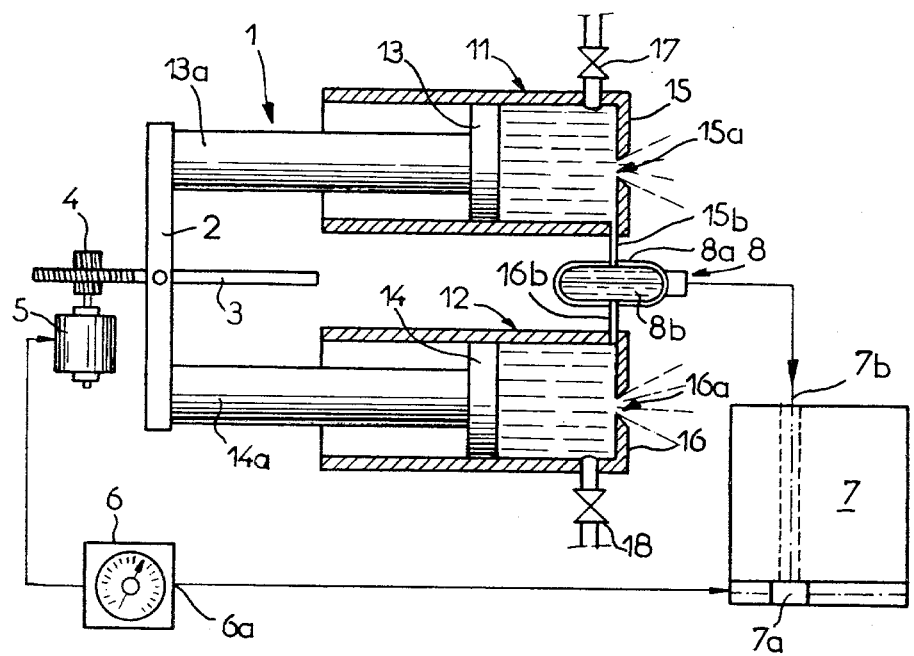
FIG. 1 is a general schematic representation of the apparatus according to the invention.

According to the embodiment chosen and shown in FIG. 1, the apparatus comprises a rheometric assembly 1 made up of two cylinders 11 and 12 having parallel axes and the same dimensions. Two pistons 13 and 14 whose respective shafts 13a and 14a are connected at one end by a crossbar 2 can slide in cylinders 11 and 12. The cylinders 11 and 12 are closed at their ends by transverse walls 15, 16 which are bored with flow orifices 15a and 16a, respectively. These orifices 15a and 16a are carefully calibrated to be as identical as possible and to have a "thin wall" orifice shape which is known in fluid mechanics technology.

Immediately upstream of the walls 15, 16 are small diameter conduits 15b and 16b which are respectively connected to two opposite chambers 8a and 8b of differential manometer 8. Furthermore, cylinders 11 and 12 are provided with filling tubes having blocking valves 17 and 18. Beyond these valves 17 and 18 the tubes communicate with distinct fluid reservoirs, not shown.

The crossbar 2 which connects piston shafts 13a and 14a is integral with rack 3 which extends parallel to the axes of cylinders 11 and 12. This rack 3 is driven by pinion 4 wedged on the shaft of motor 5. The motor is equipped with a speed control device 6, capable of subjecting the speed of rotation of motor 5 to predetermined values spread over an extended range. The control device has a control output 6a driving an XY plotter 7 at its input 7a of the X control, while the output measurement of differential manometer 8 drives input 7b of the Y control of plotter 7.

To carry out the determinations of rheological parameters of a viscoelastic fluid, for example of a dilute solution of polyethylene oxide in water, the fluid to be studied is introduced into one of the cylinders, for example the cylinder 11, across valve 17. Simultaneously introduced into cylinder 12, across valve 18 is, a Newtonian comparison fluid constituted preferably of the same solvent, in this case water, having a solute added, such as glycerine, which is known to be added to the solvent solutions having Newtonian behavior. The quantity of solute added is adjusted such that the viscosity of the comparison fluid is equal to the viscosity in Newtonian behavior of the viscoelastic fluid. It is understood that the filling of cylinders 11 and 12 is achieved by retracting pistons 13 and 14 simultaneously by a rearward motion of motor 5; before any measurement is made the cylinders 11 and 12 are purged to evacuate all air. To verify the equality of the viscosities in Newtonian behavior of the fluids filling cylinders 11 and 12, the minimal speed of motor 5 is controlled in the direction of pressure of pistons 13 and 14, and and the differential manometer 8 is seen to be in equilibrium. This signifies that the flows across orifices 15a and 16a, which are equal because pistons 13 and 14 advance at the same speed with an equal cross-section, are the position of pressure losses having equal magnitudes, the pressure downstream of the flows in free jets being the atmospheric pressure. It is clear that if differential manometer 8 is not in equilibrium, the solute concentration of the comparison fluid in the cylinder 12 must be modified to obtain this equilibrium.

The XY plotter 7 is then placed in operation, and, by virtue of action on control device 6, the speed of motor 5 is increased by discrete values. For each speed value, after establishment of a steady state, a point is plotted on plotter 7. Each point corresponds to a pair of correlated values, with, at the abscissa, a flow rate in linear relation to the strain rate in the flow and, as ordinates, a differential pressure in relation to the differential stresses. Particularly, with polyethylene oxides, the curve defined by the successive points constitutes a succession of two straight line segments, the first segment beginning with the origin and coinciding with the abscissa until a critical strain rate, while the second, beginning from the particular preceding point, moves away from the abscissa with a slope representative as an elongation viscosity.

Figure 2:
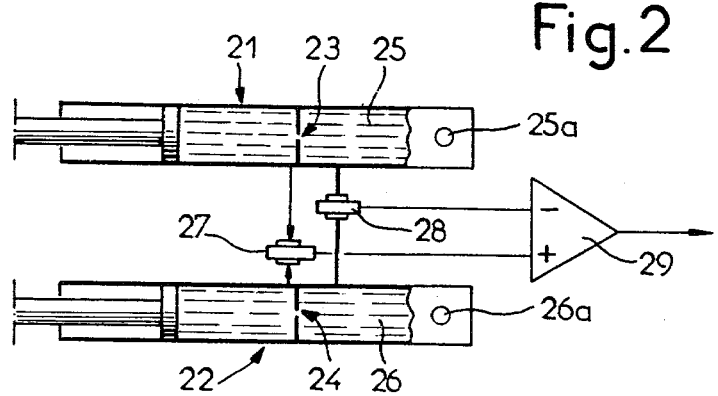
FIG. 2 schematically illustrates the arrangement with submerged jets.

The device shown schematically, seen from above in FIG. 2, is adapted to operate with a submerged jet. The cylinders 21 and 22, ended by walls where flow orifices 23 and 24 are provided, are extended axially, beyond orifices 23 and 24, via cylindrical collectors 25 and 26. The collectors are equipped with evacuation nozzles 25a and 26a situated at the upper level of the collectors 25 and 26. A first differential manometer 27 is connected between the cylinders 21 and 22 immediately upstream of orifices 23 and 24. A second differential manometer 28 is connected between the collectors 25 and 26. A differential device 29 provides an outlet signal, the difference between the output signals from manometers 27 and 28.

It will be understood that one of the cylinders, for example 21, including its collector, is filled with viscoelastic fluid, while the other is filled with Newtonian comparison fluid. The upper position of the evacuation nozzles assures that the collectors 25 and 26 are integrally filled with fluid, such that the orifices 23 and 24 are constantly submerged on the downstream side. Since it is possible that the flows of the fluids beyond the nozzles are not exactly at the same level, or that the densities of the fluids are slightly different, the downstream differential manometer 28, measuring the pressure differences downstream of the orifices, comes to bring a correcting term to the upstream pressure difference measured by the manometer 27, such that the signal issuing from the device 29 is exactly representative of the pressure difference due to the flows across the orifices (abnormal pressure).

Figure 3:
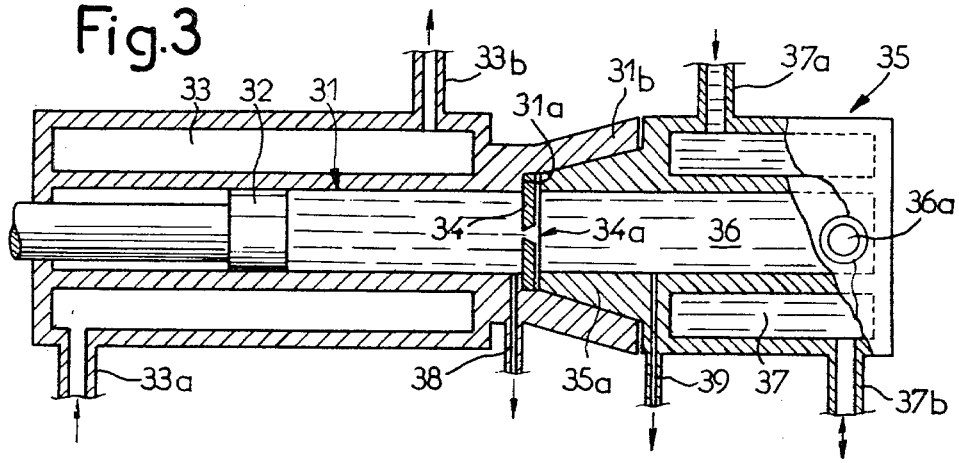
FIG. 3 is a more detailed view of a cylinder provided with a collector.

FIG. 3 illustrates in a more detailed fashion one of the two cylinders of a device provided to work with a free jet or with a submerged jet, in cross section taken along a horizontal plane passing through the axis of the cylinder. Cylinder 31, in which piston 32 can slide, is provided with an annular peripheral jacket 33, having an input tube 33a. At the end of the cylinder 31 a removeable diaphragm 34, in which is arranged having flow orifice 34a bored therein. This diaphragm 34 is maintained in abutment against shoulder 31a of the cylinder 31 by means not shown but which are easily envisioned. Beyond shoulder 31a, the cylinder flares into a machined female cone 31b. It should be noted that immediately upstream of diaphragm 34 a pressure tap 38 is provided for the connection of the upstream differential manometer.

A collector 35 is engaged by insertion of machined male cone 35a in female cone 31b. The collector 35 comprises collection chamber 36, in the axial extension of the cylinder 31, and is surrounded by jacket 37, with a small inlet tube 37a and a small outlet tube 37b. The chamber 36 comprises an evacuation nozzle 36a and a pressure tap 39 for the connection to the differential downstream manometer. Within jackets 33 and 37 a liquid can be circulated which has a temperature adjusted by a thermostatic device (not shown), liquid entering via tube 33a and passing through small tubes 33b to 37a by a flexible tube, such that the cylindrical assembly 31 and collector chamber 36 are maintained at a constant temperature equal to that of the other cylinder of course.

The collector 35 is orientable about the axis of cylinder 31 by the clearance of the generally conical or frustoconical engagement between cones 31b and 35a, such that nozzle 36a can be directed vertically upwardly or downwardly. In the first case, a submerged jet is used, and in the second case a free jet is used, the liquid thus flowing via nozzle 36a without filling chamber 36. One then realizes that the pressure tap 39 is inoperable. It will be noted, furthermore, that with a submerged jet, pressure taps 38 and 39 are both at the level of flow orifices 34a so as not to introduce hydrostatic pressure error.

Figure 4A:
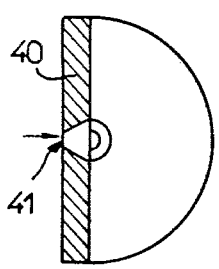
FIGS. 4A, 4B and 4C are planar and cross-sectional representations of different shapes of an orifice.
Figure 4B:
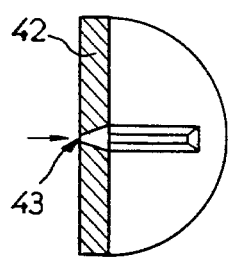
Figure 4C:
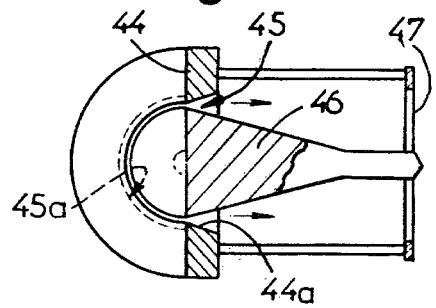

One can utilize diaphragms with this device comprising orifices having various shapes, the most important of which are shown in FIGS. 4A through 4C, in cross section and half view from the end. In FIG. 4A, a circular orifice 41 is illustrated which flares across diaphragm 40 to simulate a thin wall orifice. The strain rate is thus proportional to the ratio of the longitudinal speed of the fluid to the inlet region of the orifice, the longitudinal speed being considered as the quotient of the flow rate over the cross section.

FIG. 4B illustrates an orifice in the form of a slit 43 which flares across diaphragm 42. Here again, while neglecting the end effects which are minimized when the length of the slit is very great in comparison with its width, the strain rate is proportional to the ratio of the longitudinal speed to the half width of the slit. This shape is desirable for certain types of fluids which necessitate measurements at very low strain rate values.

The annular orifice 45 shown in FIG. 4C is substantially equivalent to the slitted orifice of FIG. 4B from the point of view of strain rate reduction at a given given flow rate, but it does not have the same end effects. In diaphragm 44 a frustoconical member 45a flares in the direction of the passage of the fluid (from left to right in the figure). Centered in hole 45a is a frustoconical insert 46 which retracts in the direction of the fluid passage and which is integrally attached to rear of the diaphragm 44 by means of support mounting 47 such that its large base is flush with the front face of diaphragm 44. It will be understood that the flaring of the annular orifice along the direction of passage of the fluid, resulting from the reciprocal arrangement of cones 44a and 46, results in a localization of the maximum strain rate in the inlet plane of the orifice, while the narrowing cross-section of the cone 46 avoids significantly disturbing of the flow downstream of the diaphragm. However, it is preferable to use the annular submerged jet orifice, to avoid disturbances due to the asymmetrical flow of a free jet under the insert.

Figure 5:
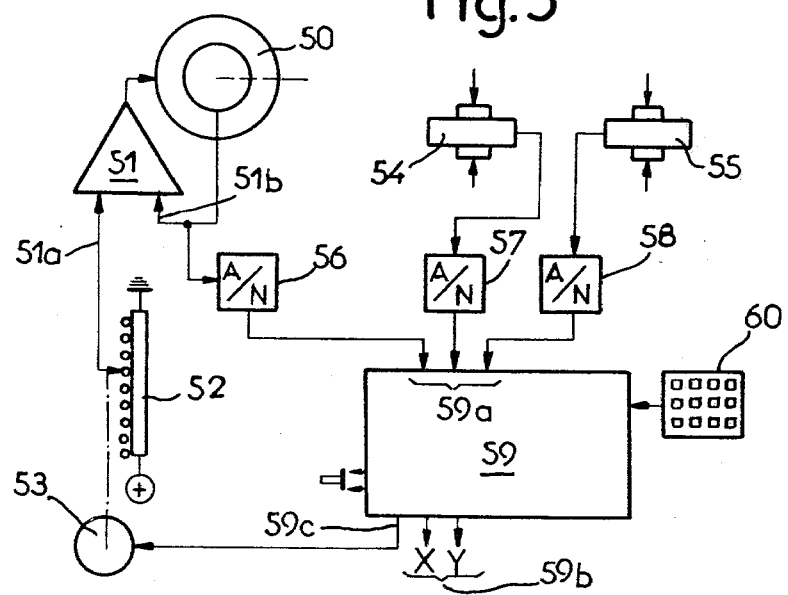
FIG. 5 is a schematic representation of control and measurement devices.

To facilitate the use of the apparatus according to the invention, the control devices can be arranged as in the schematiic of FIG. 5. The motor 50, which controls the stroke of the pistons, is fed across a conventional servo-amplifier 51 with an input 51a for a speed instruction signal and an input 51b for a tachometric signal leaving a detector connected to the motor 50. The speed instruction signal leaves a step potentiometer 52, whose slide contact is displaceable under the action of step motor 53. The tachometric signal on the input 51b is addressed equally to an analog-numerical converter 56. The output signals of the upstream and downstream differential manometers 54 and 55 (corresponding to the manometers 27 and 28 of FIG. 2) are respectively directed to the analog-numerical converters 57 and 58, respectively. A pilot calculator 59 receiives at its data inputs 59a the numerical output signals of the analog-numeric converters 56, 57 and 58, substracts the number leaving the converter 58 from that leaving the converter 57 and places the representative result of a stress in a memory location. Furthermore, the computer 59 applies to the number coming out of the converter 56 a coefficient, introduced to the digit key strip 60, representative of the ratio of the cross sections of the orifice and of the cylinder divided by the transverse dimension of the orifice, to classify a number representative of a strain rate at the corresponding instant in a memory location having an address correlated with that of the memory location representative of the stress, this operation being carried out according to the rhythm of an internal clock. Furthermore, the computer can send, on order, clock sequence signals to step motor 53, by output 59c and make the numbers representative of the strain rate and of the stress appear on the outputs 59b by reading the corresponding memory locations. The outputs 59b can be connected to an XY plotter having conventionally arranged numerical control of.

For a normal measurement, potentiometer 52 is adjusted to deliver a minimal speed signal, and without activation of the outlets 59b and 59c the numerical stress signal (signal 58 minus signal 57) is verified as being zero, or at least small and zero on the average, this value being obtained by adjustment of the viscosity of the Newtonian comparison fluid. After this adjustment, outlets 59b and 59c are blocked such that the step motor 53 causes an increase in discrete values of the speed signal. After a sufficient delay to permit the speed of the motor 50 to become stabilized at the signal value, the numeric signals furnished by the analog-numeric converters 56-58 are picked up. The numbers calculated and placed in memory thus appear for reading at outlets 59b, while motor 53 causes an increase of the speed signal.

It will be noted further that the step motor 53 and potentiometer assembly 52 can be replaced in an equivalent fashion by a numerical counter piloting a numerical analog converter, so as to process a speed signal having discrete increases.

The studies of rheological properties in flows having a high elongation component of certain viscoelastic fluids, such as those obtained by dissolution of polyethylene oxides in water, have shown that at a given concentration and temperature, abnormal pressures appear for critical strain rates and increase proportionally to the strain rate beyond the critical value. This behavior conforms to a model according to which the molecules extend beyond a strain rate substantially equal to the inverse of the temperature of relaxation of the macromolecular composition in solution. The molecules will also extend themselves in a preferential direction close to that corresponding to the principle strain rate. The fashion in which the molecules extend beyond the critical rate defines different types of responses (abnormal pressures as a function of the strain rate). In the case of polyethylene oxide solutions this response is linear. According to the concentration and the nature of the polymer (e.g., molecular structure and ionic characteristics) and the nature and quality of the solvent, one can envision different responses differing to greater or lesser degrees from the linear behavior described.

The apparatus according to the invention makes it possible to directly separate effects of a viscoelastic nature from purely viscous effects and is thus particularly adapted for use in precise, rapid and systematic research of characteristic parameters of viscoelastic fluids, and in particular of dilute, semi-dilute and concentrated solutions of macromolecular compositions which have linear or non-linear responses in a flow having a high component of elongation.

The invention thus opens a wide field of applications to all fields in which viscoelastic anomalies occur as well as in fundamental or applied research relative to molecular structures in domains where the prediction of viscoelastic behavior is of value.

Of course, the invention is not limited to the examples of the embodiments described, but includes all alternative means of execution.

We claim:

1. Apparatus adapted to determine representative parameters of rheological properties of viscoelastic liquids, particularly dilute solutions of macromolecular compositions, said apparatus including means for translating the difference between the behavior of said liquids during flow and beyond a critical strain rate with the behavior of a Newtonian liquid having a viscosity equal to that of the viscoelastic liquid ascertaining by the relationship between strain rate and the resulting stress in the two liquids, said appartus comprising:
  (a) a pair of similar cylinders each terminating at one end in a calibrated thin wall orifice;
  (b) a pair of pistons adapted to slide within the cylinders and adapted to be pushed conjointly towards the ends of the cylinders by a motor;
  (c) blockable filling means connecting each of said cylinders to a respective reservoir of liquid, one of said reservoirs adapted to hold a viscoelastic liquid and the other of said reservoirs adapted to hold a Newtonian comparison liquid;

(d) first differential pressure measurement means including two conduits, each of said conduits opening into a respective one of said cylinders immediately upstream of one of said calibrated end orifices;

(e) control means coupled to said motor to adjust its speed upwardly along a predetermined increasing range of speeds selected such that the strain rate of the liquid flow in each of the calibrated orifices has a minimal speed which is lower than and a maximum speed which is several times greater than the critical strain rate of the viscoelastic liquid; and (f) registration means for correlating respective data couples gathered from the control means and from the first differential pressure measurement means, the entire registered dats representing the relationship between the differential stress and the strain rate.

2. Apparatus according to claim 1 further comprising a cylindrical collector extending from each cylinder beyond each calibrated orifice, said collector including a liquid evacuation nozzle positionable both at the top and at the bottom of said collector, a second differential pressure measurement means being connected between the collectors.

3. Apparatus in accordance with claim 2 in which each of said cylinders has a generally horizontal axis and each of said collectors is orientable about the axis of a respective cylinder and can be reoriented such that each evacuation nozzle can assume either one of said positions with respect to the collector.

4. Apparatus in accordance with claim 2, wherein said first differential pressure measurement means comprises a first differential manometer and said second differential pressure measurement means comprises a second differential manometer.

5. Apparatus in accordance with claim 2 wherein each of said collectors has a generally frustoconical portion adapted to engage a mating frustoconical shoulder on a respective one of said cylinders.

6. Apparatus in accordance with claim 2 wherein said collector includes opposed, outwardly extending pressure taps.

7. Apparatus in accordance with claim 2 in which said registration means comprise analog/numeric converters respectively coupled to said control means, to said first and to said second differential pressure measurement means, memory means coupled to said converters and reading and display means coupled to said memory means.

8. Apparatus in accordance with either of claims 1 or 2 further comprising a jacket positioned about each of said cylinders, said jacket having a temperature regulated fluid circulating therein.

9. Apparatus in accordance with either of claims 1 or 2 in which each of said calibrated orifices is provided within a removeable diaphragm mounted at one end of each of said cylinders.

10. Apparatus in accordance with claim 9 in which each of said orifices has a circular cross-section.

11. Apparatus in accordance with claim 9 in which each of said orifices has a rectangular, elongated cross-section.

12. Apparatus in accordance with claim 9 in which each of said orifices has an annular cross-section, each of said diaphragms comprising a central frustoconical hole and a frustoconnical insert positioned within the hole which is separated from the hole by a respective one of said orifices.

13. Apparatus in accordance with claim 1 in which said control means coupled to said motor comprises a programming element adapted to define a sequence of piston velocities having discretely increasing values.

14. Apparatus in accordance with claim 1 in which said registration means comprise analog/numeric converters which are respectively coupled to said control means and to said first differential pressure measurement means, memory means coupled to said converters and reading and display means coupled to said memory means.

15. Apparatus in accordance with claim 1 wherein said cylinders are positioned along parallel axes.

16. Apparatus in accordance with claim 1 wherein said pistons are connected by a crossbar.

17. Apparatus in accordance with claim 16 wherein said crossbar is attached to a rack driven by said motor.

18. Apparatus in accordance with claim 1 wherein said blockable filling means comprise filling tubes and valves.

19. Apparatus in accordance with claim 1 wherein said control means comprise speed control means and an XY plotter is connected to said control means and to said first differential pressure measurement means.

20. Apparatus in accordance with claim 1 wherein said cylinders are indentical.

21. A method for determining representative parameters of rheological properties of viscoelastic liquids, particularly dilute solutions of macromolecular compositions, the method utilizing which apparatus includes means for translating the behavioral difference between said viscoelastic liquids during flow and beyond a critical strain rate with the behavior of a Newtonian liquid having a viscosity equal to that of the viscoelastic liquids by relating the strain rate and the resulting stress of the two liquids, the method comprising:

(a) filling one cylinder with a viscoelastic fluid and a second cylinder with a Newtonian comparison fluid;

(b) conjointly forcing said fluids through said cylinders in the same direction by driving a piston within each of said cylinders;

(c) drawing a portion of the fluid from each of cylinders upstream and adjacent to an orifice positioned at an end of each of said cylinders;

(d) conducting said fluid portions into a first differential pressure measurement means;

(e) verifying the equality of the viscosity of said fluids by assuring that said differential pressure measurement means is in equilibrium;

(f) increasing the speed of a motor with control means for driving said pistons by discrete, predetermined amounts; and (g) plotting a point corresponding to a pair of correlated values derived from said first differential pressure measurement means and said control means.

22. A method in accordance with claim 21 further comprising taking a second differentiial pressure measurement by a second differential pressure measurement means and correcting the value determined by the first differential pressure measurement means.

* * * * *

UNITED STATES PATENT AND TRADEMARK OFFICE
CERTIFICATE OF CORRECTION

PATENT NO. : 4,316,383
DATED : February 23, 1982
INVENTOR(S) : Daniel FRUMAN et al.

It is certified that error appears in the above—identified patent and that said Letters Patent is hereby corrected as shown below:

Column 2, line 45, "behavior of" should be --behavior for--.
Column 5, line 17, delete "and" (third occurrence).
Column 5, line 42, "as" should be --of--.
Column 6, line 46, delete "the".
Column 7, line 18, delete "of".
Column 7, line 58, delete "of".
Column 9, line 19, "dats" should be --data--.

Signed and Sealed this

Eighth Day of June 1982

|SEAL|

Attest:

Attesting Officer

GERALD J. MOSSINGHOFF
Commissioner of Patents and Trademarks